(12) United States Patent
Rios et al.

(10) Patent No.: US 8,060,212 B1
(45) Date of Patent: Nov. 15, 2011

(54) EXTERNAL MEDICAL DEVICE CONFIGURATIONS FOR COMMUNICATING WITH IMPLANTABLE MEDICAL DEVICES

(75) Inventors: Ronald R. Rios, Thousand Oaks, CA (US); Gregory C. Bevan, Canyon Country, CA (US); Eliot L. Ostrow, Sunnyvale, CA (US); Armando M. Cappa, Granada Hills, CA (US); Allan R. Schwartz, Moorpark, CA (US); George L. Walls, Valencia, CA (US)

(73) Assignee: Pacesetter, Inc., Sylmar, CA (US)

( * ) Notice: Subject to any disclaimer, the term of this patent is extended or adjusted under 35 U.S.C. 154(b) by 510 days.

(21) Appl. No.: 11/736,425

(22) Filed: Apr. 17, 2007

(51) Int. Cl.
*A61N 1/02* (2006.01)

(52) U.S. Cl. ............ 607/60; 128/903; 128/904; 607/30; 607/31; 607/32; 607/59

(58) Field of Classification Search .................... 607/27, 607/30–32, 60, 59; 128/903–904; 379/106.02
See application file for complete search history.

(56) References Cited

U.S. PATENT DOCUMENTS

| 6,167,312 A * | 12/2000 | Goedeke ........................ 607/60 |
| 6,985,088 B2 * | 1/2006 | Goetz et al. .............. 340/870.07 |
| 2002/0007198 A1 * | 1/2002 | Haupert et al. ................. 607/30 |
| 2002/0183819 A1 * | 12/2002 | Struble ........................ 607/122 |
| 2004/0010290 A1 * | 1/2004 | Schroeppel et al. ............. 607/3 |
| 2004/0044369 A1 * | 3/2004 | Roy ................................ 607/4 |
| 2005/0203582 A1 * | 9/2005 | Healy et al. .................... 607/31 |
| 2006/0020302 A1 * | 1/2006 | Torgerson et al. ............. 607/60 |
| 2006/0030901 A1 * | 2/2006 | Quiles et al. .................... 607/60 |
| 2006/0030903 A1 * | 2/2006 | Seeberger et al. ............. 607/60 |
| 2006/0142820 A1 * | 6/2006 | Von Arx et al. ................ 607/60 |
| 2006/0265540 A1 * | 11/2006 | Mass et al. .................... 710/305 |

* cited by examiner

*Primary Examiner* — Carl H Layno
*Assistant Examiner* — Jennifer Stewart (57) ABSTRACT

Exemplary external medical devices are configurable to communicate with an implantable medical device (IMD). One medical device includes multiple IMD telemetry ports operable to connect IMD telemetry mechanisms to the medical device. The medical device also includes a control unit configured to control the IMD telemetry mechanisms.

13 Claims, 6 Drawing Sheets

EXTERNAL MEDICAL DEVICE CONFIGURATIONS FOR COMMUNICATING WITH IMPLANTABLE MEDICAL DEVICES

FIELD OF THE INVENTION

The subject matter presented herein generally relates to external medical devices configurable to communicate with implantable medical devices.

BACKGROUND

Implantable medical devices (IMDs) exist in the marketplace to treat a range of patient conditions. For example, various IMDs are utilized to address cardiac-related conditions. External medical devices, such as programmers, are utilized to communicate with the IMDs. For instance, during an implantation procedure data can be transferred between the external medical device and the IMD. In some cases, operational data (i.e., instructions) can be transmitted from the external medical device to the IMD and data gathered by the IMD can be transmitted to the external medical device.

External medical devices are often manifested as a housing that protects a control or processing unit for processing the IMD related data. The external medical device can also include a telemetry mechanism for facilitating data transfer with the IMD or alternatively the external medical device can include a telemetry mechanism port for connecting to the telemetry mechanism. In various scenarios having a capacity to connect to only a single telemetry mechanism diminishes the performance of the external medical device and/or unnecessarily increases the time required to perform a procedure with the external medical device.

SUMMARY

Exemplary external medical devices configurable to communicate with an implantable medical device (IMD) as well as related methods and systems are described. One external medical device includes multiple IMD telemetry ports operable to connect IMD telemetry mechanisms to the external medical device. The external medical device also includes a control unit configured to control the IMD telemetry mechanisms.

An exemplary method queries IMD telemetry mechanisms connected to an external medical device. The method also ascertains functionalities related to the IMD that can be achieved on the external medical device based at least in part on results of said querying.

BRIEF DESCRIPTION OF THE DRAWINGS

Features and advantages of the described implementations can be more readily understood by reference to the following description taken in conjunction with the accompanying drawings. In the description that follows, like numerals or reference designators will be used to reference like parts or elements wherever feasible.

DETAILED DESCRIPTION

Overview

Various exemplary techniques, methods, devices, systems, etc., described herein pertain to external medical devices configurable to communicate with an implantable medical device (IMD). The present implementations offer a functionality that allows the external medical device to communicate with the IMD via multiple IMD telemetry mechanisms. In some cases, the external medical device includes multiple IMD telemetry ports through which multiple IMD telemetry mechanisms can be connected to the external medical device. In other cases, some or all of the multiple IMD telemetry mechanisms can be built into or otherwise permanently connected to the external medical device. These implementations offer enhanced functionality over existing configurations where only a single IMD telemetry mechanism can be connected to the external device and the IMD telemetry mechanism must be disconnected to allow another different IMD telemetry mechanism to be connected to the external device.

First Exemplary System

Figure 1:
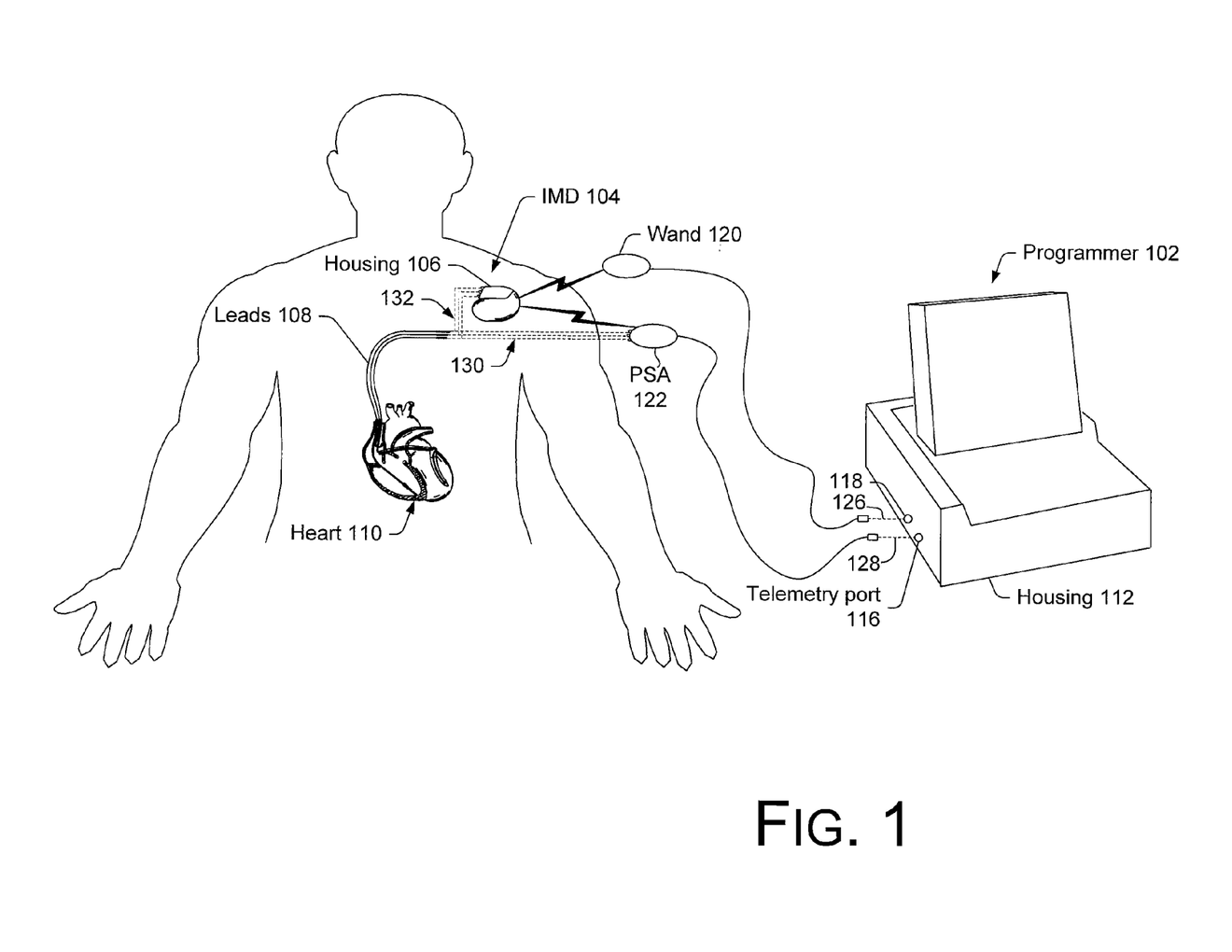
FIGS. 1-6 are system diagrams that illustrate exemplary configurations for communicating with an implantable medical device in accordance with one implementation.

FIG. 1 illustrates an exemplary external medical device manifested as programmer 102 configurable to communicate with an implantable medical device (IMD) 104. In this instance, IMD 104 functions as an implantable cardioverter/defibrillator (ICD) that includes a housing 106 that can be attached to leads 108. The leads 108 are positioned proximate the patient's heart 110 and extend to the housing 106 which is positioned in a more convenient (i.e., less intrusive) location such as the patient's pectoral pocket. In other instances, an IMD such as an ICD can be implemented as a single integrated unit rather than separate components.

Figure 7:
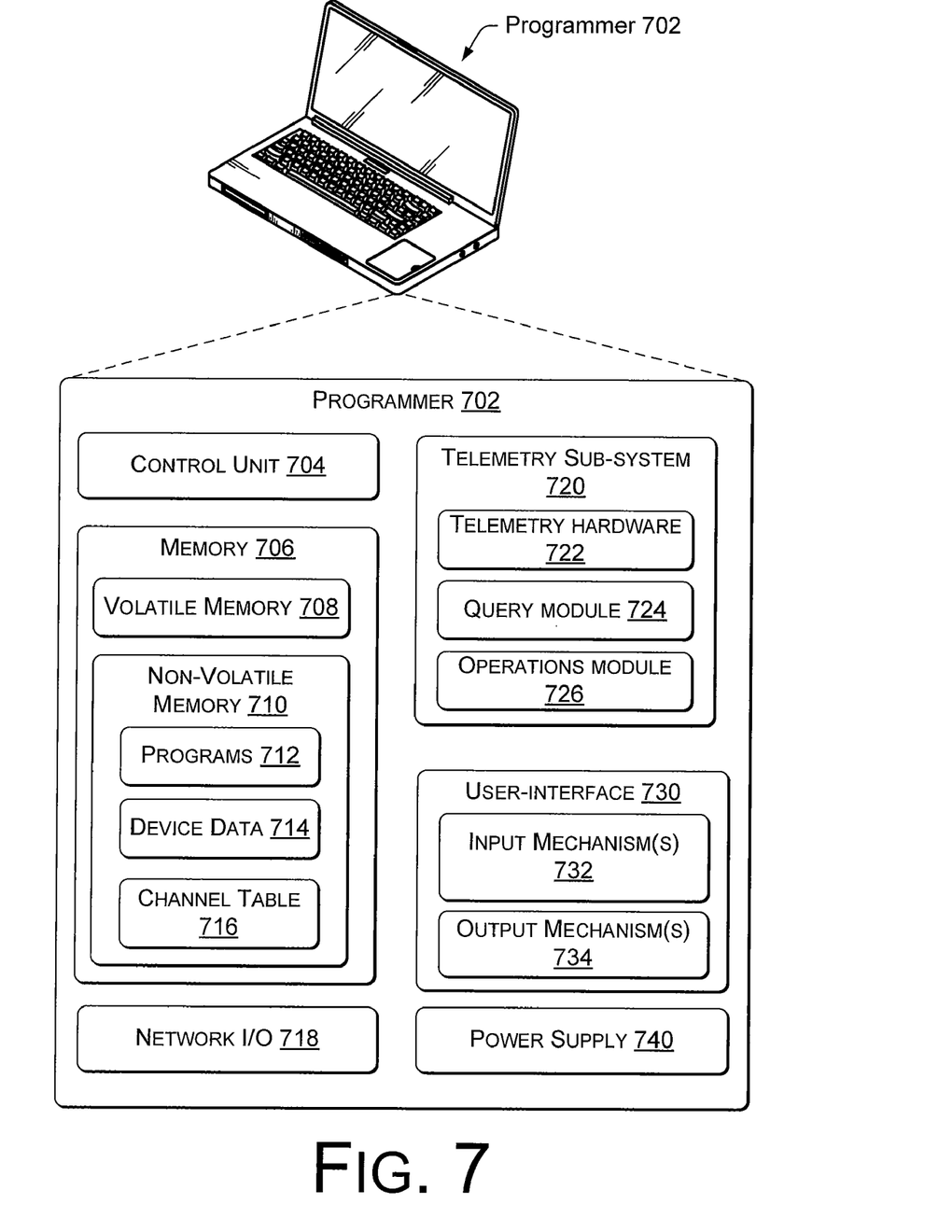
FIG. 7 is a functional block diagram of an exemplary external medical device illustrating basic elements that are operable to communicate with an implantable medical device in accordance with one implementation.

In this implementation programmer 102 includes a housing 112 for protecting a processing or control unit (specifically designated FIG. 7). The control unit is configured to process IMD-related data that may be received from or sent to the IMD 104. Programmer 102 further includes multiple IMD telemetry ports; with two IMD telemetry ports 116, 118 specifically designated. Individual IMD telemetry ports 116, 118 allow an IMD telemetry mechanism to be connected to external medical device 102. In this case, the telemetry mechanisms are manifested as a telemetry wand (hereinafter "wand") 120, and a pacing system analyzer (PSA) 122.

Wand 120 functions to interrogate the IMD 104 and transfer data between the programmer 102 and the IMD. Generally the wand allows two way communications with the IMD, but one way communication could be utilized such as where the wand receives data from the IMD, but does not transmit data to the IMD. The PSA 122 can provide some or all of the functionality of wand 120. Alternatively or additionally, PSA 122 can be connected to the IMD leads 108 during implantation to assess lead performance. Stated another way, the PSA when connected to the IMD leads 108 allows programmer 102 can mimic IMD functions to test lead placement.

The following example serves to illustrate the enhanced functionality offered by programmer 102 in an implantation setting. In this example, during implantation wand 120 is connected to IMD telemetry port 118 as indicated by dashed line 126 and PSA 122 is connected to IMD telemetry port 116 as indicated by dashed line 128.

During implantation of IMD 104, the physician makes an incision and places leads 108 in the heart 110. The physician wants to ensure the distal end of the leads positioned in the heart 110 are in good locations in relation to pacing threshold, sensed signals, and interference, among others. For instance, the placement of the leads can produce undesired consequences during pacing. In some cases, the placement can cause pacing pulses to inadvertently stimulate the phrenic nerve which can give the patient hiccups and/or other undesired affects. Leads 108 are connected to PSA 122 as indicated by dashed lines 130. (In some cases, a set of additional leads and/or connectors can be utilized to interconnect the leads 108 and the PSA 122.) The PSA 122 emulates (to various degrees) the functionality of IMD 104 to test lead placement. While the physician is working on lead placement, a clinician can utilize wand 120 to check that IMD 104 is functioning properly before the IMD is implanted. The programmer can readily perform both IMD interrogation through wand 120 and lead placement analysis through PSA 122 without any need to disconnect or reconnect either of the wand or PSA.

Once the physician is satisfied with the placement of the leads 108 the leads are disconnected from the PSA 122 and connected to IMD housing 106 as indicated by dashed lines 132. Wand 120 can then be utilized to interrogate the IMD 104 without having to disconnect PSA 122 from programmer 102. For instance, the programmer can analyze data obtained from IMD 104 and customize software instructions for operation on the IMD based upon the obtained data. The customized software instructions can then be transmitted to the IMD via wand 120. If lead dislodgement occurs or if the physician is not happy with the performance of the IMD, the lead placement can be adjusted and the leads 108 can be reconnected to the PSA 122 while the wand 120 remains available for interrogating the IMD 104. Further, in an instance where an IMD telemetry port such as IMD telemetry port 116 should fail, programmer 102 can remain functional via IMD telemetry port 118.

Second Exemplary System

Figures 2, 3, 4:
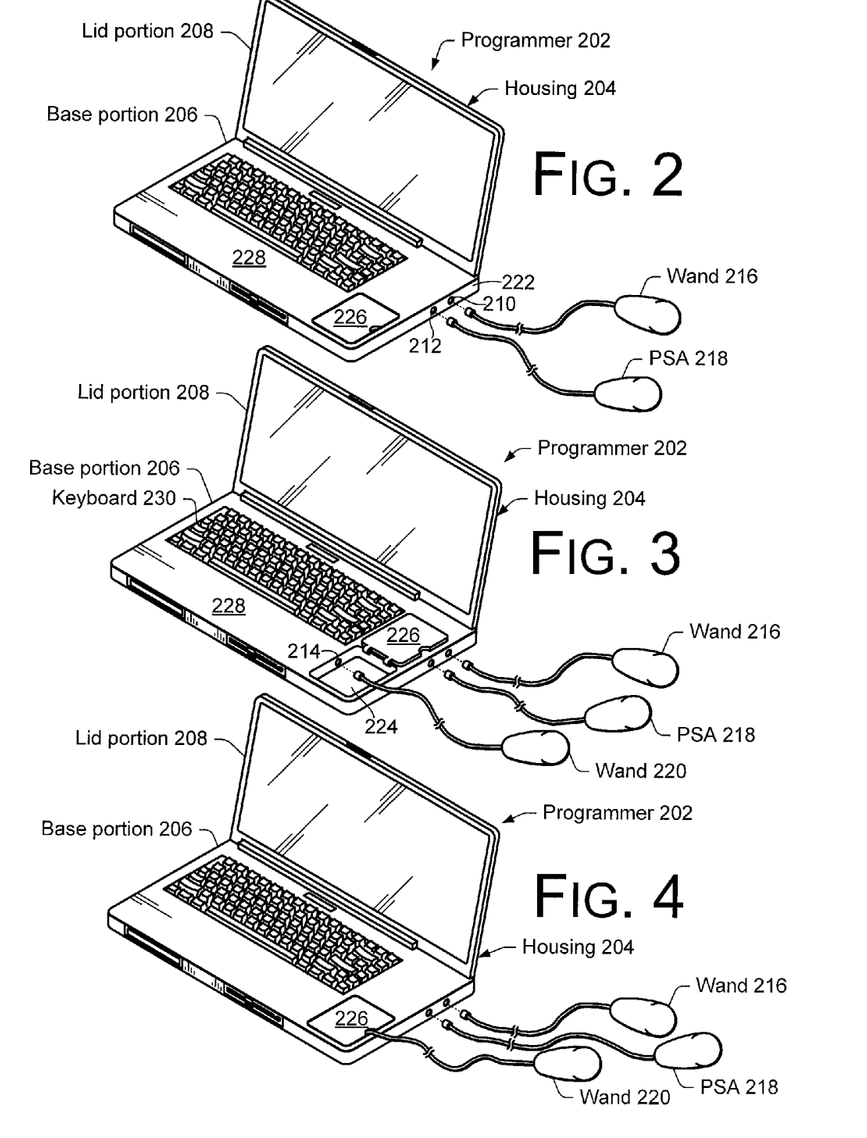

FIGS. 2-4 collectively illustrate another exemplary programmer 202 configurable to communicate with an implantable medical device (not specifically designated). Programmer 202 is protected by a housing 204 that includes a base portion 206 and a lid portion 208 hingedly deployable relative to the base portion 206. In this instance, programmer 202 includes 3 IMD telemetry ports 210, 212, and 214 that are connected to an IMD telemetry wand 216, a PSA 218, and an IMD telemetry wand 220, respectively. In this implementation, wands 216, 220 can be either inductive or radio frequency (RF) wands.

In this case, IMD telemetry ports 210, 212 are positioned on an external surface 222 of housing 204 and are accessible regardless of a position of lid portion 208. Stated another way, IMD telemetry ports 210, 212 are accessible whether the lid portion 208 is open or closed. Conversely, in this case IMD telemetry port 214 is accessible only when lid portion 208 is open as illustrated in FIGS. 2-4.

In this implementation, IMD telemetry port 214 is located on a surface of housing 204 that partially defines a storage volume or storage bay 224 (FIG. 3). The storage bay is further defined by a lid 226 that when closed forms part of a surface 228 through which a keyboard 230 extends. Lid 226 when open as illustrated in FIG. 3 lays flat against surface 228 and does not obstruct keyboard 230. In this instance, lid 226 includes a hinge mechanism that is not exposed on surface 228 when lid 226 is closed. The hinge mechanism runs parallel to surface 228 and is slideable in a direction that is orthogonal to surface 228. Lid 226 further includes a configuration that allows the lid to be fully closed with wand 220 deployed from IMD telemetry port 214. The storage bay 224 allows storage of wand 220 within the programmer's housing so that the wand can remain with the programmer thereby increasing user convenience.

For purposes of explanation consider the following implantation related scenario that illustrates at least some of the advantages of programmer 202. In this scenario in preparation for surgical implantation of an IMD, a clinician can connect wand 216 that in this example is sterile and suitable for use in a surgical sterile field to IMD telemetry port 210 and connect PSA 218 to IMD telemetry port 212. The clinician can open lid 226, deploy wand 220 from storage bay 224 and close lid 226. Rather than using sterile wand 216, the clinician can utilize wand 220 to interrogate the IMD. For instance, the clinician can check the IMD's battery strength, among other functions. The clinician can then put wand 220 back into storage bay 224. Sterile wand 216 is thereby reserved for use in the patient's sterile field.

During implantation PSA 218 is available to test lead placement in the patient and wand 216 is simultaneously available to interrogate the IMD in the patient's sterile field. Further, should wand 216 fail for some reason, wand 220 is also simultaneously connected to the programmer and could be utilized without having to reconfigure programmer 202. Further, upon completion of the implantation procedure, wand 216 and PSA 218 can be disconnected from programmer 202 and the programmer wheeled with the patient to recovery. The programmer remains functional at all times since wand 220 is stored in storage bay 224 and can be utilized to interrogate the IMD while stored and/or is easily deployed for use. In either case, the programmer is ready for use without going and looking for a suitable wand that would then need to be connected to the programmer before use.

Third Exemplary System

Figure 5:
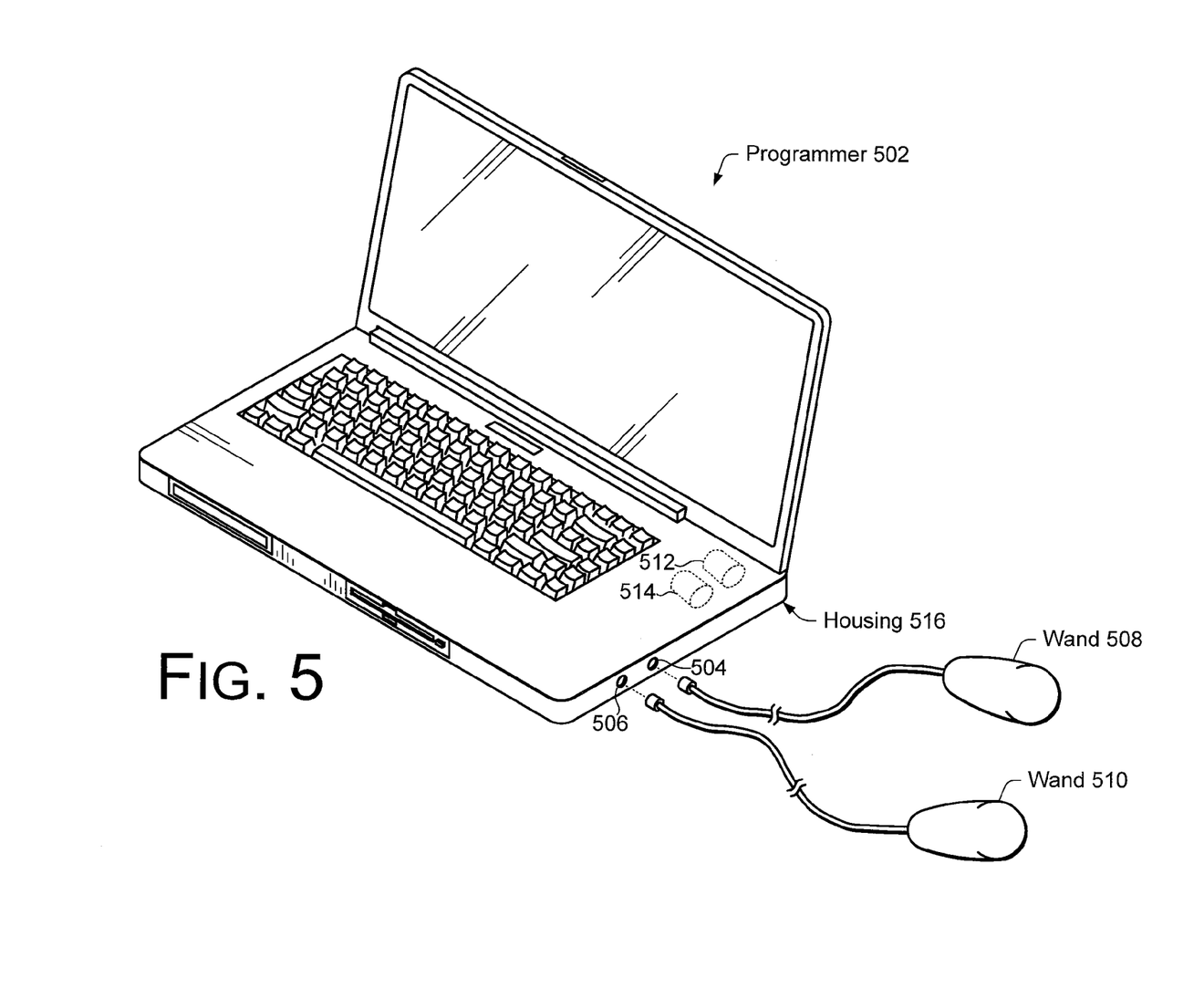

FIG. 5 illustrates another programmer 502 that has multiple IMD telemetry ports 504, 506 for receiving IMD telemetry mechanisms such as wand 508 and wand 510. Programmer 502 also includes multiple additional IMD telemetry mechanisms. In this configuration the multiple additional IMD telemetry mechanisms are manifested as two wireless radio frequency (RF) IMD telemetry mechanisms 512, 514. In this case, the IMD telemetry mechanisms 512, 514 are built into the programmer 502. The IMD telemetry mechanisms 512, 514 are contained within programmer housing 516 and are therefore shown in dashed "ghost" lines as they would not normally be visible in the illustrated view.

The IMD telemetry mechanisms 512, 514 offer the convenience of being completely wireless, but may not offer the versatility of IMD telemetry mechanisms connected to IMD telemetry ports 504, 506. For example, wands 508, 510 are readily positioned proximate the patient and therefore may utilize inductive transmission or RF transmission whereas the IMD telemetry mechanisms 512, 514 are more constrained to meet increased transmission distances. Further, wands 508, 510 are readily replaced if enhanced technologies become available and/or upon wand failure. Further, as mentioned above, either of wands 508, 510 can be removed and replaced by other IMD telemetry mechanisms, such as a PSA.

Fourth Exemplary System

Figure 6:
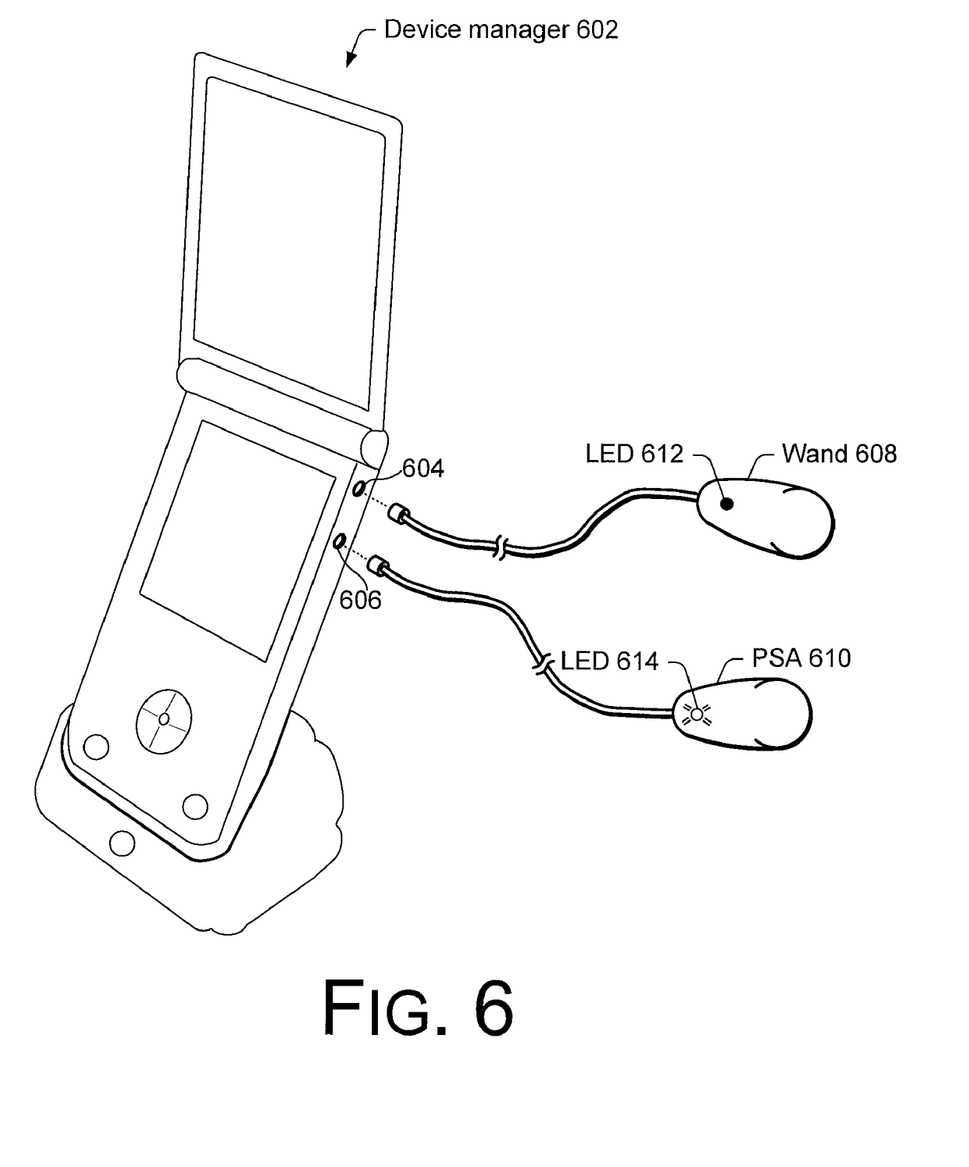

FIG. 6 illustrates another external medical device that has a form factor of a device manager 602. The device manager has multiple IMD telemetry ports 604, 606 for receiving IMD telemetry mechanisms such as a wand 608 and a PSA 610. In this instance, both wand 608 and PSA 610 are equipped with light emitting diodes (LEDs) 612, 614 respectively. The LEDs 612, 614 can be utilized by device manager 602 to convey information to a user. For instance, in this case LED 614 is illuminated (i.e., 'on') indicating that PSA 610 is presently interrogating an IMD. In contrast, LED 612 is not illuminated (i.e., 'off') indicating that wand 608 is not currently performing any interrogation functions. In another implementation, the LED of a telemetry mechanism can be illuminated whenever the telemetry mechanisms is connected to and recognized by the device manager. Further, a blinking LED can indicate that a respective telemetry mechanism is presently interrogating an IMD. So for instance, in the present example, when wand 608 and PSA 610 are connected to device manager 602 and detected by the device manager's control unit the control unit can cause respective LEDs 612, 614 to be illuminated. If a clinician requests a PSA functionality be performed through a user-interface of the device manager, then the control unit can cause LED 614 to blink when PSA 610 is performing the requested function while LED 612 continues to be steadily illuminated. The skilled artisan should recognize other implementations consistent with the concepts described above and below.

Exemplary External Medical Device Architecture

FIG. 7 describes functional components of an exemplary external medical device in the form of a programmer 702 in more detail. The described components can also be implemented in other external medical device configurations such as device manager 602 described in relation to FIG. 6, among others. The skilled artisan should recognize other components that are compatible with the concepts described above and below. In this instance, programmer 702 includes a processing or control unit 704 and memory 706. The control unit 704 controls operations carried out by the programmer 702, such as programming an IMD, gathering data from the IMD, and/or carrying out various testing or diagnostic functions. Memory 706 includes both volatile memory 708 (e.g., RAM) and non-volatile memory 710 (e.g., ROM, EEPROM, Flash, disk, optical discs, persistent storage, etc.).

Programs, operating parameters, and algorithms 712, which are used in controlling the programming and testing functions, may be stored in memory 706. When a program is running, various instructions are loaded into volatile memory 708 and executed by control unit 704. Device data or IMD-related data 714 collected from the IMD may be stored in memory 706 for subsequent analysis and/or transfer to other computing systems.

In this particular configuration, a channel table 716 can also be maintained in the non-volatile memory 708. This table lists the various channels that the programmer may use to communicate with an IMD. For instance, a first telemetry mechanism associated with the programmer can utilize a first available channel from the table while a second telemetry mechanism associated with the programmer can utilize a second available channel from the table. The table can also track which of the channels are available for use and which are being used by other external medical devices such as other programmers.

The programmer 702 may further be equipped with a network I/O connection 718 to facilitate communication with a network and/or other computing devices such as a server(s). The network I/O 718 may be a wire-based connection (e.g., network card, modem, etc.) or a wireless connection, such as a Bluetooth device.

The programmer 702 is equipped with a telemetry sub-system 720 that manages communications between programmer 702 and an IMD. The telemetry sub-system 720 includes telemetry hardware 722, a query module 724 and an operations module 726. The telemetry hardware 722 can include multiple IMD telemetry ports through which IMD telemetry mechanisms can be connected to the programmer and/or the IMD telemetry mechanisms themselves. Various examples of IMD telemetry ports and IMD telemetry mechanisms are described above. The telemetry hardware 722 can also include a switch(s) that allows the telemetry sub-system to access a desired IMD telemetry port and/or telemetry mechanism.

The query module 724 functions to query the telemetry hardware to ascertain a current system configuration. For instance, the query module can query each IMD telemetry port to determine what, if any, IMD telemetry mechanism is connected to each IMD telemetry port. Other implementations may query directly to IMD telemetry mechanisms regardless of how individual IMD telemetry mechanisms are connected to the programmer.

The operations module 726 receives information from the query module 724 about the IMD telemetry ports and/or IMD telemetry mechanisms and ascertains a present system configuration from the information. For instance, consider a hypothetical system where the query module supplies information to the operations module that presently one telemetry wand is connected to the programmer. The operations module then ascertains that the programmer can provide wand functionality for a user, but cannot provide PSA functionality. The telemetry sub-system 720 in cooperation with programs 712 implemented by control unit 704 can cause a user-perceptible signal to be generated indicating the present system configuration. For instance, a display can be generated on a user-interface (introduced below) that indicates which functionalities are presently enabled.

The programmer 702 may also include a user interface 730 which includes one or more user input mechanism(s) 732 and one or more output mechanisms 734. Input mechanisms allow user input to be received by the programmer. Examples of mechanisms for user input include, but are not limited to (e.g., keypads, buttons, selection wheels, touch pad, touch screen or touch-sensitive screen, voice recognition system, etc.). Output mechanisms 734 allow information to be provided from the programmer for user observation. The output mechanisms generate signals such as audio and/or visual signals for the user which, for example, can relate to a patient condition associated with the IMD. Examples of output mechanisms include, but are not limited to, monitors, LCDs, speakers, etc. For purposes of characterization, distinct input and output mechanisms are described, but in some instances, a single mechanism performs both functions. For instance, the user interface can be manifested as a touch-sensitive screen which performs both input and output functions.

The components illustrated in FIG. 7 are interconnected via one or more buses (not shown) and are powered by a power supply 740. Additionally, various aspects of the methods and systems described throughout this disclosure may be implemented in computer software or firmware as computer-executable instructions. The instructions can be stored on any computer-readable storage media. When executed, these instructions direct the programmer to perform various functions and tasks described above and below.

Operation

Figure 8:
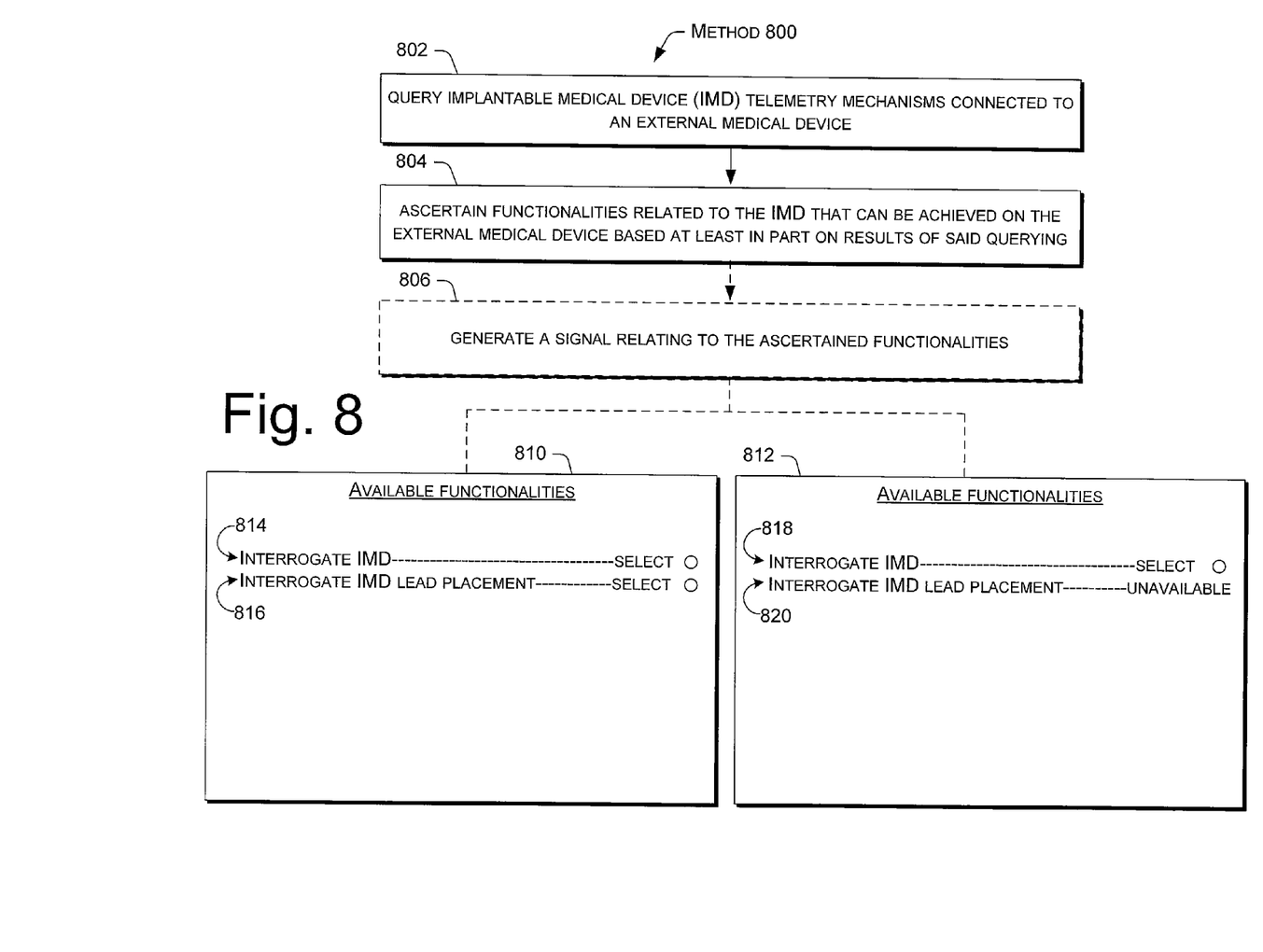
FIG. 8 is a flowchart of an exemplary method for determining a configuration for communicating with an implantable medical device in accordance with one implementation.

FIG. 8 shows an exemplary method or technique 800 for determining an external medical device's configuration for interrogating an implantable medical device (IMD). This method 800 may be implemented in connection with any suitably configured external medical devices and/or systems of external medical devices and IMDs. Non-limiting examples of devices and/or systems upon which the method can be implemented are described above in relation to FIGS. 1-7. Method 800 includes blocks 802-804. An additional block 806 offers an example of an action that can be taken with results obtained from performing method 800. The order in which the method is described is not intended to be construed as a limitation, and any number of the described blocks can be combined in any order to implement the method, or an alternate method. Furthermore, the methods can be implemented in any suitable hardware, software, firmware, or combination thereof such that a computing device can implement the method. In one case, the method is stored on a computer-readable storage media as a set of instructions such that execution by a computing device, such as an external medical device, causes the computing device to perform the method.

At block 802, implantable medical device (IMD) telemetry mechanisms connected to an external medical device are queried. In one instance, IMD telemetry ports are queried for connected IMD telemetry mechanisms. In another instance, all system devices can be queried to identify available IMD telemetry mechanisms.

At block 804, the method ascertains functionalities related to the IMD that can be achieved on the external medical device based at least in part on results of said querying from block 802. In some instances, once IMD telemetry mechanisms are identified at block 802, individual IMD telemetry mechanisms are further queried to determine the IMD interrogation functionality that the individual IMD telemetry mechanisms can perform. Various technologies are available for the IMD telemetry mechanisms to convey information regarding their respective capability. For example, in one implementation IMD telemetry mechanisms contain a resistor. The value of the resistor is representative of the type and therefore functionality of the specific IMD telemetry mechanism. The external device can contain a reference table that correlates resistor values to telemetry mechanism types. In one case, a queried IMD telemetry mechanism may be a wand that utilizes induction to transfer data with the IMD. Another queried IMD telemetry mechanism may be a wand that utilizes radio frequency (RF) signals to transfer data with the IMD. Still another queried IMD telemetry mechanism may be a pacing system analyzer (PSA) wand capable of transferring data via induction and/or being physically connected to leads to evaluate lead placement.

Block 806 represents an example of an action that can be taken with the information obtained by performing blocks 802 and 804. Block 806 generates a signal relating to the ascertained functionalities. For instance, the signal can relate to causing an identified IMD telemetry mechanism to perform an interrogation function. In another example the signal can relate to generating a user-interface that conveys the identified functionalities. Two such examples are evidenced as user-interface screen shots 810, 812. Assume for purposes of explanation that in the example of screen shot 810, two IMD telemetry mechanisms were identified. The first identified IMD telemetry mechanism is a wand that has basic IMD interrogation functionality. The second identified IMD telemetry mechanism is a PSA that has basic IMD interrogation functionality and lead placement interrogation functionality. Screen shot 810 indicates at line 814 that IMD interrogation is available and can be selected by a clinician. Further, screen shot 810 indicates at line 816 that IMD lead placement interrogation is also available and can be selected by a clinician. In contrast, assume that in relation to screen shot 812 only a wand was identified via method 800. In this case, screen shot 812 indicates on line 818 that IMD interrogation is available and can be selected by a clinician. However, line 820 indicates that IMD lead placement evaluation is unavailable and the clinician cannot select that feature. The skilled artisan should recognize other implementations consistent with the concepts described above and below.

Conclusion

Exemplary techniques, methods, devices, systems, etc., relating to external medical devices configurable to communicate with implantable medical devices (IMDs) are described above. The present implementations offer a functionality that allows the external medical device to communicate with the IMD via multiple IMD telemetry mechanisms. In some cases, the external medical device includes multiple IMD telemetry ports through which multiple IMD telemetry mechanisms can be connected to the external medical device. In other cases, some or all of the multiple IMD telemetry mechanisms can be built into or otherwise permanently connected to the external medical device. Although techniques, methods, devices, systems, etc., have been described in language specific to structural features and/or methodological acts, it is to be understood that the subject matter defined in the appended claims is not necessarily limited to the specific features or acts described. Rather, the specific features and acts are disclosed as exemplary forms of implementing the claimed methods, devices, systems, etc.

What is claimed is:

1. An external medical device comprising:
   multiple IMD telemetry ports each operable to connect a plurality of different types of implantable medical device (IMD) telemetry mechanisms to the medical device;
   a control unit configured to control the IMD telemetry mechanisms and to generate a graphical user interface identifying presently enabled functionalities of the IMD telemetry mechanisms physically attached to the medical device via individual IMD telemetry ports of the multiple IMD telemetry ports;
   a telemetry sub-system coupled to the control unit and configured to query the multiple IMD telemetry ports to identify the types of IMD telemetry mechanisms connected to the multiple IMD telemetry ports; and
   wherein the graphical user interface further identifies presently disabled functionalities of the IMD telemetry mechanisms physically attached to the medical device.

2. The medical device of claim 1, further comprising an IMD telemetry port switch that is controllable by the control unit for selecting individual IMD telemetry ports to communicably couple to the control unit.

3. The medical device of claim 1, embodied as one of: a device manager and a programmer.

4. A medical device comprising:
   a control unit configured to process data related to an implantable medical device (IMD);
   at least one IMD telemetry port for removeably connecting an IMD telemetry mechanism to the medical device;
   a telemetry sub-system coupled to the control unit and configured to query the at least one IMD telemetry port to identify types of telemetry mechanisms connected to the at least one IMD telemetry port;
   at least one different IMD telemetry mechanism built into the medical device;
   a switch mechanism for selectively communicatively coupling one of the IMD telemetry mechanism and the other different IMD telemetry mechanism to the control unit, wherein the control unit is configured to generate a graphical user interface identifying presently enabled functionalities of the IMD telemetry mechanisms physically attached to the medical device; and
   wherein the graphical user interface further identifies presently disabled functionalities of the IMD telemetry mechanisms physically attached to the medical device.

5. The medical device of claim 4, wherein the graphical user-interface displays an indication of the identified IMD telemetry mechanism and the at least one different IMD telemetry mechanism and allows a user to select one of the identified IMD telemetry mechanism and the at least one different IMD telemetry mechanism for interrogating the IMD.

6. The medical device of claim 4, wherein the graphical user interface allows a user to select an interrogation procedure and the control unit is further configured to select one of the IMD telemetry mechanism and the at least one different IMD telemetry mechanism for accomplishing the interrogation procedure.

7. The medical device of claim 4, wherein the control unit is configured to cause a user-perceptible signal to be generated that indicates which of the IMD telemetry mechanism and the at least one different IMD telemetry mechanism are currently performing an interrogation procedure.

8. An external medical device comprising:
   a control unit configured to process data related to an implantable medical device (IMD); and,
   multiple IMD telemetry mechanisms configured to transfer the data between the control unit and the IMD, the IMD telemetry mechanisms each indicating to a telemetry sub-system a type of functionality specific to each IMD telemetry mechanism;
   wherein the control unit is configured to generate a graphical user interface identifying presently enabled functionalities of the IMD telemetry mechanisms physically attached to the medical device and wherein the graphical user interface further identifies presently disabled functionalities of the IMD telemetry mechanisms physically attached to the medical device.

9. The medical device of claim 8, wherein a first of the IMD telemetry mechanisms is configured to transfer the data via radio frequency (RF) signals and wherein a second of the IMD telemetry mechanisms is configured to transfer the data via induction.

10. The medical device of claim 8, wherein a first of the IMD telemetry mechanisms is configured to transfer the data wirelessly and wherein a second of the IMD telemetry mechanisms is configured to be physically connected to the IMD.

11. The medical device of claim 8, wherein a first of the IMD telemetry mechanisms is configured to transfer the data wirelessly and wherein a second of the IMD telemetry mechanisms is configured to be physically connected to one or more IMD leads.

12. The medical device of claim 8, wherein at least one of the IMD telemetry mechanisms is built into the medical device.

13. The medical device of claim 8, wherein at least one of the IMD telemetry mechanisms is built into the medical device and at least one other of the IMD telemetry mechanisms is removeably connected to the medical device via an IMD telemetry port.

* * * * *